(12) United States Patent
Soboleski (10) Patent No.: US 9,235,892 B2
(45) Date of Patent: Jan. 12, 2016

(54) METHOD AND DEVICE FOR COMPARING RADIOGRAPHIC IMAGES

(75) Inventor: Donald A. Soboleski, Ontario (CA)

(73) Assignee: Denise De Andrade Castro, Ontario (CA)

( * ) Notice: Subject to any disclaimer, the term of this patent is extended or adjusted under 35 U.S.C. 154(b) by 159 days.

(21) Appl. No.: 14/007,409

(22) PCT Filed: Mar. 30, 2012

(86) PCT No.: PCT/CA2012/000271
§ 371 (c)(1),
(2), (4) Date: Sep. 25, 2013

(87) PCT Pub. No.: WO2012/129653
PCT Pub. Date: Oct. 4, 2012

(65) Prior Publication Data
US 2014/0016852 A1    Jan. 16, 2014

Related U.S. Application Data

(60) Provisional application No. 61/470,212, filed on Mar. 31, 2011.

(51) Int. Cl.
*A61B 6/00* (2006.01)
*G06T 5/00* (2006.01)
*G06T 7/00* (2006.01)

(52) U.S. Cl.
CPC .............. *G06T 7/0014* (2013.01); *A61B 6/502* (2013.01); *A61B 6/5211* (2013.01); *A61B 6/5294* (2013.01); *A61B 6/582* (2013.01); *G06T 5/007* (2013.01); *G06T 2207/10116* (2013.01)

(58) Field of Classification Search
CPC .......... A61B 6/482; A61B 6/12; A61B 6/484; H05G 1/26
See application file for complete search history.

(56) References Cited

U.S. PATENT DOCUMENTS

| 4,233,507 A | 11/1980 | Volz |
| 4,941,164 A | 7/1990 | Schuller et al. |
| 6,684,097 B1 * | 1/2004 | Parel .................. A61N 5/0601 |
| | | 378/98.11 |
| 2003/0095695 A1 | 5/2003 | Arnold |
| 2005/0152615 A1 | 7/2005 | Hutchinson et al. |
| 2010/0130832 A1 | 5/2010 | Lang et al. |
| 2010/0278409 A1 | 11/2010 | Wiemker et al. |
| 2012/0319686 A1 * | 12/2012 | Jesmanowicz ........ A61B 5/055 |
| | | 324/309 |

FOREIGN PATENT DOCUMENTS

| EP | 1 417 931 A1 | 12/2004 |
| FR | 2 622 714 B1 | 5/1989 |
| WO | WO 98/19272 | 5/1998 |

(Continued)

*Primary Examiner* — Vu Le
*Assistant Examiner* — Kenny Cese
(74) *Attorney, Agent, or Firm* — Saliwanchik, Lloyd & Eisenschenk (57) ABSTRACT

The present disclosure provides a method of standardizing a digital radiographic medical image, including obtaining a digital radiographic image of a variable attenuation plate to provide at least one reference value of at least one image characteristic, such as optical density and contrast, and standardizing the digital radiographic medical image against the reference values. Also provided are methods for comparing two or more radiographic images including standardizing the images against at least one reference value of at least one image characteristic obtained from a digital radiographic image of a variable attenuation plate.

11 Claims, 5 Drawing Sheets

(56) References Cited

FOREIGN PATENT DOCUMENTS

| WO | WO 02/17789 A2 | 3/2002 |
| WO | WO 2004/019256 A2 | 3/2004 |
| WO | WO 2006/033712 A1 | 3/2006 |
| WO | WO 2009/060346 A2 | 5/2009 |
| WO | WO 2011/003390 A1 | 1/2011 |

* cited by examiner

FIG. 6

METHOD AND DEVICE FOR COMPARING RADIOGRAPHIC IMAGES

CROSS REFERENCE TO A RELATED APPLICATION

This application is a National Stage Application of International Application Number PCT/CA2012/000271, filed Mar. 30, 2012; which claims benefit of U.S. Provisional Application Ser. No. 61/470,212, filed Mar. 31, 2011; both of which are incorporated herein by reference in their entirety.

BACKGROUND

The present disclosure relates to methods and devices for comparing and standardizing the appearance of radiographic images. More specifically, the present disclosure relates to methods and devices for using a variable attenuation plate (VAP) to aid in the interpretation of radiographs and to facilitate the comparison of radiographic images taken on different occasions.

Radiographic imaging is a common diagnostic tool used routinely in the health care system and is vital in patient care throughout the world. X-rays are a form of high energy electromagnetic radiation which can be attenuated, absorbed or scattered to varying extents by all materials, including tissues found in the human body. In general, a radiographic image is obtained by directing a beam of X-rays toward the appropriate area or part of a patient's body. A detector (which can be a film-based cassette or a digital detector) placed on the opposite side of the region being examined is then 'exposed' by the X-rays that have passed through the body tissues. Some structures such as bone have a higher density and will allow little if any of the X-ray beam to reach the detector. Other less dense tissues such as air-filled lungs will only minimally attenuate the beam, allowing most of the X-rays to pass through and reach the detector. Soft tissues, including organs such as heart and liver, will show an attenuation between that of bone and that of air. The resulting radiographic image formed on the detector therefore shows variations in intensity of exposure depending on the density of the body structures and tissues through which the X-ray beam has passed. The image can then be analyzed and interpreted by radiologists or other physicians.

The quality of a radiographic image depends on many variables. For example, the energy of the photons in the X-ray beam (as controlled by the peak kilovoltage (kVp) setting of the X-ray generator) affects the ability of the beam to penetrate body tissues. If the energy of the beam is too high, there will not be a sufficient difference between the ability of various body tissues to attenuate the beam, and the contrast of the resulting image will be reduced. As well, the intensity or quantity of photons in the beam (as controlled by the mA (milliamperes) or mAs (mA·s, milliampere seconds) setting of the X-ray generator), along with the exposure time, will affect the intensity as well as the contrast of the resulting image. A more intense X-ray beam will need less exposure time to provide an image of sufficient intensity. Optimal settings for a good quality image, including kVp and mA or mAs settings, are generally chosen depending upon the type of tissue being visualized. In addition, the patient needs to be properly positioned in the X-ray beam and as still as possible. Care needs to be taken to avoid exposing regions of the body or materials such as clothing, catheters, etc. that will attenuate portions of the X-ray beam, resulting in a change in the exposure of the underlying detector and thus a change in appearance of the radiographic image. For example, the extent to which the abdomen or shoulder is included when taking a chest radiograph will affect the exposure of the image obtained. Radiographs are often over- or underexposed due to inadequate control of these variables.

With the advent of digital imaging and increasingly powerful computer programs, radiologists and other health providers can now routinely manipulate digital radiographic images manually using Picture Archiving and Communication Systems (PACS), so as to optimize differences in the attenuation and contrast between body structures, and to attempt to equalize images of a patient taken on different occasions so as to facilitate comparison. Because some body structures will be better visualized with 'darker', more contrasted images while others are better visualized with 'lighter', less contrasted images, the manual adjustment of the density and contrast of digital images, or "windowing", is a very useful tool in the routine interpretation of radiographs. However, digital adjustment of images can lead to potential inconsistency in reporting because manipulation of the images is generally based on the personal preferences of individual interpreters. For example, two different radiologists interpreting the same image may window the radiographic image differently and thus come to different conclusions, and the image alterations made by one radiologist may not be available to the other for comparison or assessment. A recent study of 6 health care professionals interpreting chest radiographs has shown that there can be a 50% or higher rate of disagreement as to whether the disease process being examined was improving or deteriorating.

As an example, chest radiographs are routinely performed to diagnose fluid in the lungs (congestion). Normally, lung tissue weakly attenuates an X-ray beam because of the air contained within it, and therefore provides a relatively dark radiograph image. As the air is replaced by fluid in a more congested lung, the X-ray beam is more strongly attenuated, resulting in a 'whiter' radiographic appearance. It can be difficult for a radiologist interpreting such a lung radiograph to know whether the "whiteness" of the image is due to increased fluid or merely due to other variable factors as described above. The problem can be compounded if the radiographic image has also been digitally manipulated, or windowed, to facilitate interpretation, as described above.

In addition, radiographic images of the same subject may be taken on two or more occasions in order to monitor the progress of a particular medical treatment. For example, follow-up radiographs for assessing healing of broken bones or follow-up chest radiographs for patients with heart or lung conditions, such as congestive heart failure, or patients undergoing cancer treatment are common. In such cases, it can be difficult to tell whether differences in the appearance of the subsequent images are due to real, medically relevant changes in the patient's condition or simply due to variations in capturing and/or processing the radiographic image at each occasion, as described above.

There is therefore a need for a method and device that will allow radiographic images to be interpreted consistently in the face of variations in the conditions under which the image is obtained. In addition, there is a need for a method and device that facilitates efficient and reliable comparison of radiographic images taken on different occasions.

SUMMARY

One aspect of the present disclosure provides a method of standardizing a digital radiographic medical image comprising obtaining a digital radiographic image of a variable attenuation plate; determining at least one reference value of at least one image characteristic, and standardizing the digital radiographic medical image against the at least one reference value.

In at least one embodiment, the at least one image characteristic is selected from optical density and contrast.

In at least one embodiment, the method involves digitally storing the at least one reference value of at least one image characteristic for use in standardizing the digital radiographic medical image.

In at least one embodiment, the method comprises programming a computer with instructions to standardize the digital radiographic medical image against the at least one reference value of at least one image characteristic.

Another aspect of the present disclosure provides a method of comparing a first radiographic medical image with a second radiographic medical image, comprising obtaining a radiographic image of a variable attenuation plate; determining at least one reference value of at least one image characteristic; and standardizing the first radiographic medical image and the second radiographic medical image against the at least one reference value of at least one image characteristic such that the first radiographic medical image can be compared to the second radiographic medical image.

In at least one embodiment, the at least one image characteristic is selected from optical density and contrast.

In at least one embodiment, the method involves digitally storing the at least one reference value of at least one image characteristic for use in standardizing the first and second radiographic medical images.

In at least one embodiment, the method comprises programming a computer with instructions to standardize the first and second radiographic medical images against the at least one reference value of at least one image characteristic.

In at least one embodiment, the method involves recording a first radiographic medical image of a patient including a first image of the variable attenuation plate; recording a second radiographic medical image of the patient including a second image of the variable attenuation plate; determining optical density and contrast reference values from the first and second images of the variable attenuation plate; and standardizing the first radiographic medical image and the second radiographic medical image against the optical density and contrast reference values such that the first radiographic medical image can be compared to the second radiographic medical image.

In at least one embodiment, the method comprises programming a computer with instructions to determine the optical density and contrast reference values from the first and second images of the variable attenuation plate and to standardize the first and second radiographic medical images against the optical density and contrast reference values.

Another aspect of the present disclosure provides a method of processing a radiographic image, comprising: recording a reference radiographic image of a variable attenuation plate, the reference radiographic image having at least one reference image characteristic; determining at least one reference value of the at least one image characteristic; storing the radiographic equipment setting and the at least one reference image characteristic as at least one preset reference value; recording a radiographic image of a patient; and processing the radiographic image of the patient using the at least one preset reference value.

In at least one embodiment, the method comprises programming a computer with instructions to equalize or normalize at least one image characteristic of the radiographic image against the preset reference values.

In another aspect, the present disclosure provides a computer-readable medium comprising instructions for programming a computer as described herein.

A further aspect of the present disclosure provides a variable attenuation plate for use in a method as described herein.

The methods described herein provide for standardization of radiographic images and for improved comparison of radiographic images taken of a patient on two or more separate occasions, by equalizing chest radiograph appearance and allowing synchronization of manual windowing with comparison studies.

BRIEF DESCRIPTION OF THE DRAWINGS

Preferred embodiments will now be described in greater detail and will be better understood when read in conjunction with the following drawings.

DETAILED DESCRIPTION OF THE EMBODIMENTS

The present disclosure provides a method of standardizing a digital radiographic medical image, comprising taking a digital radiographic image of a variable attenuation plate to provide reference values of at least one image characteristic, including but not limited to optical density and contrast, and standardizing or normalizing the digital radiographic medical image against the reference values.

The present disclosure also provides a method and device for comparing radiographic images taken over two or more occasions. In at least one embodiment, the method involves taking a radiographic image of a variable attenuation plate to provide reference values of at least one image characteristic, including but not limited to optical density and contrast, and standardizing the radiographic images against the reference values. In at least one embodiment the method involves recording a first radiographic image of a patient that includes a first image of a variable attenuation plate, recording a second radiographic image of the patient that includes a second image of the same variable attenuation plate and processing the first radiographic image and the second radiographic image such that the first radiographic image can be compared to the second radiographic image.

The variable attenuation plate has two or more attenuation regions which differ in their X-ray attenuation properties. This provides a reference marker which allows both the optical density and the contrast of images taken at different times to be compared. In at least one embodiment, these attenuation regions can be made of different materials which attenuate X-rays to different degrees, or can be made of the same material but at different thicknesses, or a combination thereof. Suitable materials for manufacturing the attenuation regions include but are not limited to metals such as aluminum, steel, gold, silver, brass, copper and titanium, and alloys of these metals.

The attenuation regions can be of any suitable shape and size to allow a clear radiographic image to be obtained. Advantageously, the attenuation regions are square in shape and have a minimum size of about 4 mm square. The materials and/or thicknesses of each attenuation region are chosen so that they will provide images whose optical densities are distinguishable from each other under the conditions typically used to record a medical radiographic image, as will be understood by the skilled person.

In at least one embodiment, the variable attenuation plate is made of two or more materials of differing X-ray attenuation, including the attenuation regions discussed above and support materials to support the attenuation regions. The support materials include but are not limited to material encasing or supporting the attenuation regions and a handle attached to the attenuation regions. In at least one embodiment, the support materials can be relatively transparent to X-rays compared to the attenuation regions. Such materials are well known to the skilled person. The variable attenuation plate can be square, circular, rectangular, polygonal, irregular, or any other convenient shape, and is advantageously flat so that the radiographic image of the plate can be easily and reliably reproduced.

In at least one embodiment, the variable attenuation plate is positioned remotely from the patient or support apparatus, but placed so that the image of the variable attenuation plate is adjacent to the image of the patient on the radiographic image. In at least one embodiment, the variable attenuation plate is placed on, or is an integral part of, a radiograph cassette, and can be placed in the margins of the cassette, so as to be consistent in placement and to facilitate comparison of radiographic images taken on different occasions. Two or more variable attenuation plates can be placed on or embedded in the radiograph cassette to improve the reliability of the method, in the event that image data from one variable attenuation plate is unusable. In this way, as will be understood by the skilled person, an image of the variable attenuation plate will be embedded in the recorded radiographic image.

In at least one embodiment, it is contemplated that the variable attenuation plate can include one or more indicia as used on well known standard X-ray markers. Such indicia can indicate the positioning of the patient or other conditions under which the radiographic image is obtained, and include but are not limited to "left" or "right". In such embodiments, a letter "L" or a letter "R" can be incorporated into the variable attenuation plate or the support material thereof. In at least one alternative embodiment, the variable attenuation plate can be manufactured in the overall shape of a letter "L" or a letter "R", among other suitable arrangements.

In at least one embodiment, the method is a computer-implemented method. Specifically designed software allows the use of one or more variable attenuation plates to equalize radiographic appearance, and allows dynamic synchronization of manual windowing when comparing a patient's recent radiographs to their previous radiographs. This equalization and synchronization method results in increased radiographic impression consistency among radiologists and results in a significant savings in reporting time.

In at least one embodiment, the method compares a first radiographic image with a second radiographic image wherein both images contain an image of the variable attenuation plate. As discussed above, the variable attenuation plate has at least two regions, and therefore provides at least two reference measurements of optical density and at least one reference measurement of contrast for each radiographic image.

In this embodiment, a first radiographic image is recorded of the subject that includes an embedded image of a variable attenuation plate as discussed above. Subsequently, a second radiographic image of the subject is recorded which also includes an embedded image of the same variable attenuation plate.

In at least one embodiment and as will be understood by the skilled person, it is contemplated that after the first radiographic image is recorded, this image may be additionally processed by a skilled professional by way of processes well known in the art, including but not limited to manual windowing. Alternatively, it is also contemplated that no manual windowing of the first radiographic image occurs subsequent to recording the image.

At least two reference measurements of optical density and at least one reference measurement of contrast can be extracted from both the first and second radiographic images of the variable attenuation plate embedded in both the first and second radiographic images. As will be understood by the skilled person, software code can be written with instructions to extract these reference values from the images of the variable attenuation plate that are embedded in each of the first and the second radiographic images.

Once the reference values of optical density and contrast have been extracted from the first and the second radiographic image, these reference values can be used to equalize or normalize optical density and contrast in the first radiographic image and the second radiographic image. Again, as will be understood by the skilled person, software can be written with instructions to equalize or normalize the optical density and contrast of the first radiographic image and the second radiographic image against the reference values of optical density and contrast.

Because a variable attenuation plate of known attenuation properties is used to obtain each image, the reference values of optical density and contrast extracted from the second radiographic image can be directly compared with and standardized against the reference values of optical density and contrast extracted from the first radiographic image. As will be understood by the skilled person, as the reference values of optical density and contrast extracted from the image of the variable attenuation plate embedded in each radiographic image are standardized against each other, the remaining image of the subject contained in each radiographic image will also be equalized or normalized with respect to both optical density and contrast. In this way, the first radiographic image can be directly compared with the second radiographic image (or vice versa) with respect to optical density and contrast, because each image contains standard values of optical density and contrast obtained from the variable attenuation plate, which are independent of variables related to the conditions under which the images were obtained, as described above.

In addition, once the first radiographic image is equalized with the second radiographic image with respect to both optical density and contrast, both images can then be manually windowed in a synchronized manner, as will be readily understood by the skilled person. In other words, the skilled professional can manipulate both images simultaneously while keeping the measurements of contrast and optical density equalized between the two images. This allows a direct comparison between the first and second images, with respect to optical density and contrast, to be maintained while the images are simultaneously processed for improved appearance and interpretability. Furthermore, the time needed to interpret and compare the images can be reduced, thereby improving efficiency.

As will be understood by those of skill in the art, the instructions to extract the reference values from the images of the variable attenuation plate that are embedded in each of the first and the second radiographic images and the instructions to equalize or normalize the optical density and contrast of the first radiographic image and the second radiographic image against the reference values of optical density and contrast can be combined with medical image processing software including instructions for other functions, including but not limited to windowing, viewing of single images or two or more images simultaneously, and other radiographic image processing functions.

It is also contemplated that the variable attenuation plate will provide optical density and contrast measurements that can be automatically loaded into a radiographic imaging system in order to create a series of preset reference values. In this way, it is contemplated that these preset reference values could be used so that it is not necessary to include an image of the variable attenuation plates themselves when obtaining each subsequent radiographic image.

For example and as will be understood by the skilled person, a radiographic image of a variable attenuation plate can be recorded using an X-ray beam having particular settings for peak kilovoltage, measured in kilovolts (kVp) and beam intensity, measured in milliamperes (mA) or milliampere seconds (mA·s). In this embodiment, the variable attenuation plate can be imaged alone or its image can be embedded in another radiographic image, as discussed above.

Once the radiographic image of the variable attenuation plate is recorded, at least two reference values of optical density and at least one reference value of contrast can be extracted from the image of the variable attenuation plate. In this way, a series of preset reference values can be created associating the radiographic equipment settings (peak kilovoltage and milliamperage) with the characteristics of the resultant radiographic image (contrast and optical density). The following table illustrates how a set of example preset reference values could be created (note that the values included are mere algebraic placeholders and are not intended to indicate or imply any particular magnitude or mathematical relationship):

| | Radiographic Equipment Settings | | | |
|---|---|---|---|---|
| | Peak kilovoltage | Milliamperage | Preset Reference Values | |
| Preset No. | (kVp) | (mA or mA · s) | Contrast | Optical Density |
| 1 | X1 | Y1 | A1 | B1 |
| 2 | X2 | Y2 | A2 | B2 |
| 3 | X3 | Y3 | A3 | B3 |

It is contemplated that these preset reference values could be digitally stored for later recall when digitally processing a subsequent radiographic image recorded using comparable radiographic equipment settings. In this way, a radiologist analyzing and/or interpreting the image can select appropriate preset reference values against which to standardize the appearance of the subsequent radiographic image. In addition, a radiologist comparing two images of the same patient taken on different occasions can automatically select preset reference values appropriate to each image when digitally processing the radiographic images. As explained above, both images can then be manually windowed in a synchronized manner, so as to be manipulated simultaneously while keeping the measurements of contrast and density equalized between the two images. Again, as the skilled person will appreciate, software providing instructions to equalize or normalize the optical density and contrast of the subsequent radiographic image against the preset reference values of optical density and contrast can be combined with medical image processing software having other functions.

It is also contemplated that there may be one set of preset reference values which are particularly suitable for digitally processing radiographic images where details of bone structure are to be analyzed, while different sets of preset reference values may be particularly suitable for digitally processing radiographic images where details of soft tissue, including various organs, or air-filled lung tissue, for example, are to be interpreted.

Figure 1:
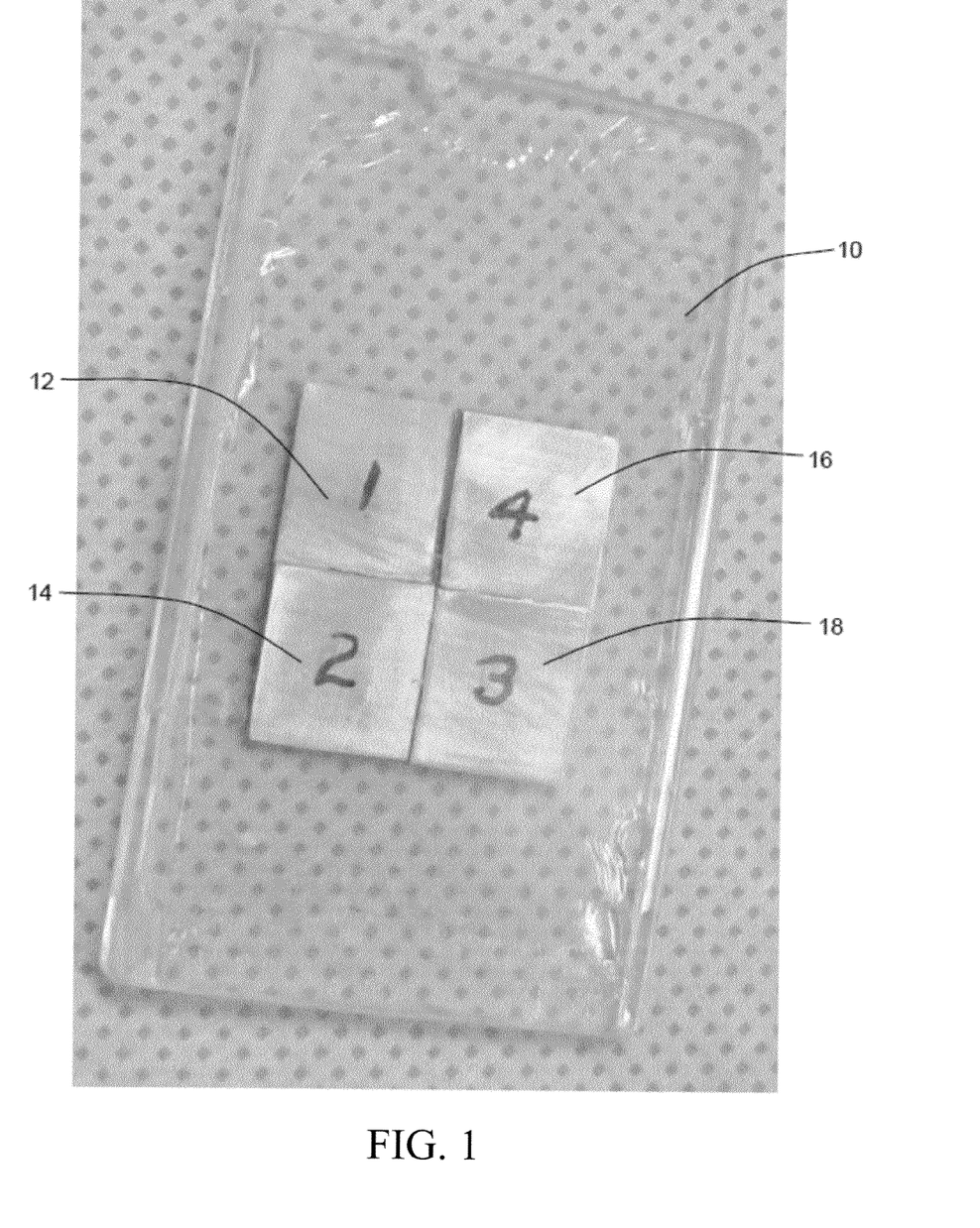
FIG. 1 is a front view of one embodiment of the present variable attenuation plate.
Figure 2:
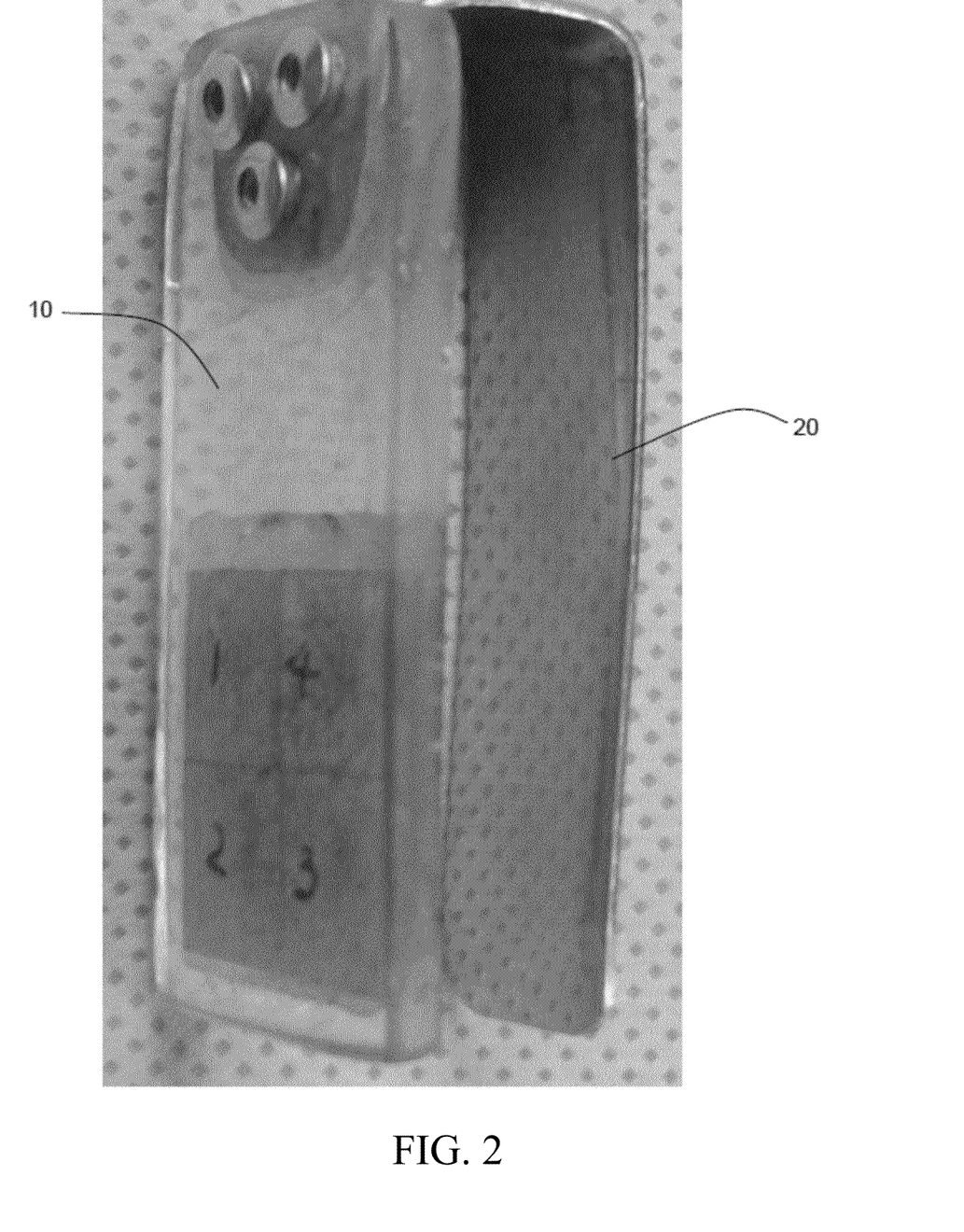
FIG. 2 is a side view of one embodiment of the present variable attenuation plate, showing a clip for attachment to a radiograph cassette.

Turning to FIGS. 1 and 2, at least one embodiment of a variable attenuation plate is shown. In at least one embodiment, variable attenuation plate 10 can have four variable attenuation regions 12, 14, 16, 18 each having differing X-ray attenuation. Variable attenuation regions 12, 14, 16, 18 can be mounted on a display plate or support material that in at least one embodiment is transparent, as will be readily understood by the skilled person in the art. It is contemplated that variable attenuation regions 12, 14, 16, 18 could be embedded within the display plate or alternatively mounted to the outside surface of the display plate.

In at least one embodiment, clip 20 is provided that can removably secure variable attenuation plate 10 to a radiographic cassette. Clip 20 can be secured to variable attenuation plate 10 by any known means, including but not limited to mechanical means such as rivets or chemical means such as an adhesive. In this way, variable attenuation plate 10 can be clipped to a radiographic cassette such that variable attenuation plate 10 is superimposed on the resulting radiographic image. In this way, an image of the variable attenuation plate is embedded within the resultant radiographic image.

Figures 3, 4A:
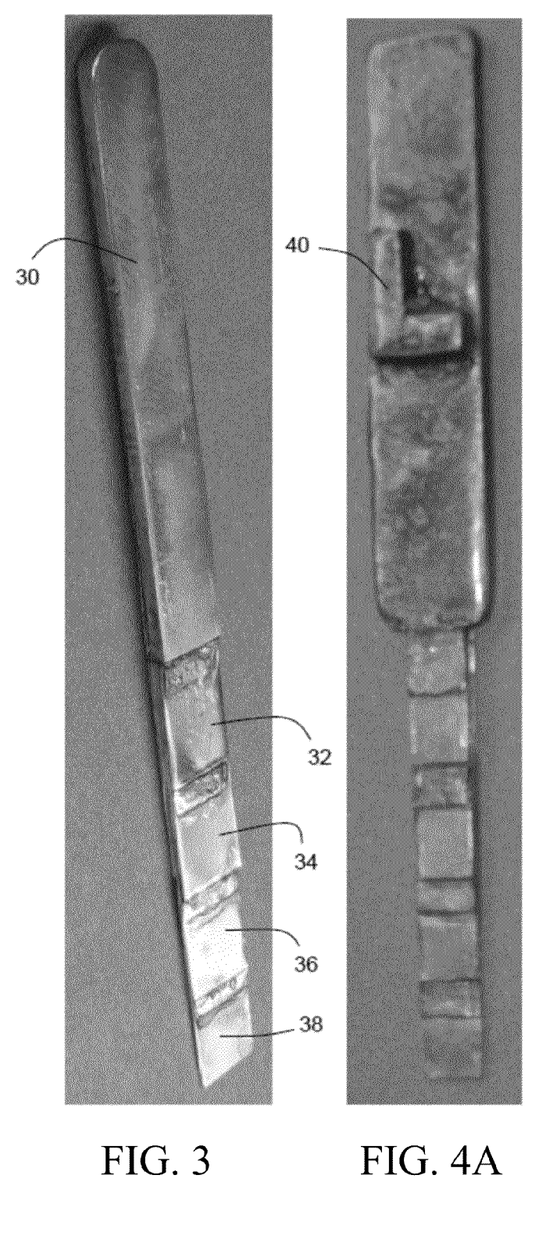
FIG. 3 is a perspective view of another embodiment of the present variable attenuation plate having a handle, showing the varying thickness of the plate.
FIG. 4A is a perspective view of another embodiment of the present variable attenuation plate, showing the varying thickness of the plate and containing a marker.

Turning to FIG. 3, another embodiment of variable attenuation plate 30 is shown. In this embodiment, it can be clearly seen that each variable attenuation region 32, 34, 36, 38 has a differing thickness, and accordingly, a different X-ray attenuation. In this embodiment, the support material is not transparent and is constructed of the same material as variable attenuation regions 32, 34, 36, 38. In this embodiment, the support material functions as a handle to be used by the radiographic equipment professional to facilitate placement of the variable attenuation plate 30.

Figure 4B:
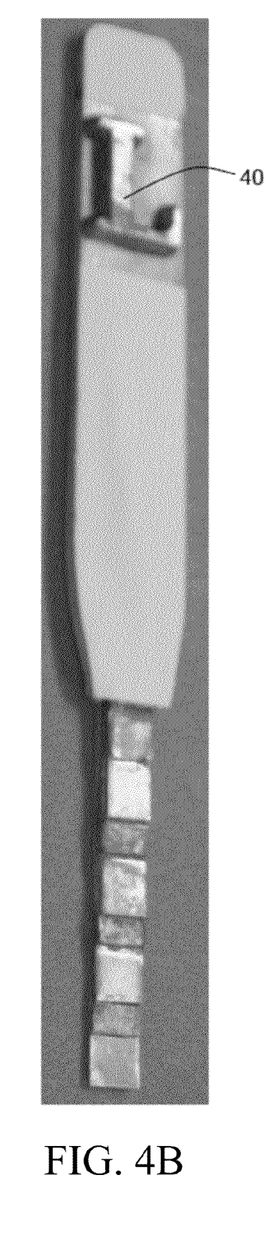
FIG. 4B is a perspective view of yet another embodiment of the present variable attenuation plate, showing the varying thickness of the plate and containing a marker.

Turning to FIGS. 4A and 4B, other embodiments of a variable attenuation plate are shown that are analogous to the embodiment shown in FIG. 3. In these embodiments, an indicium 40 shaped like a letter "L" is included on the variable attenuation plate.

Figure 5:
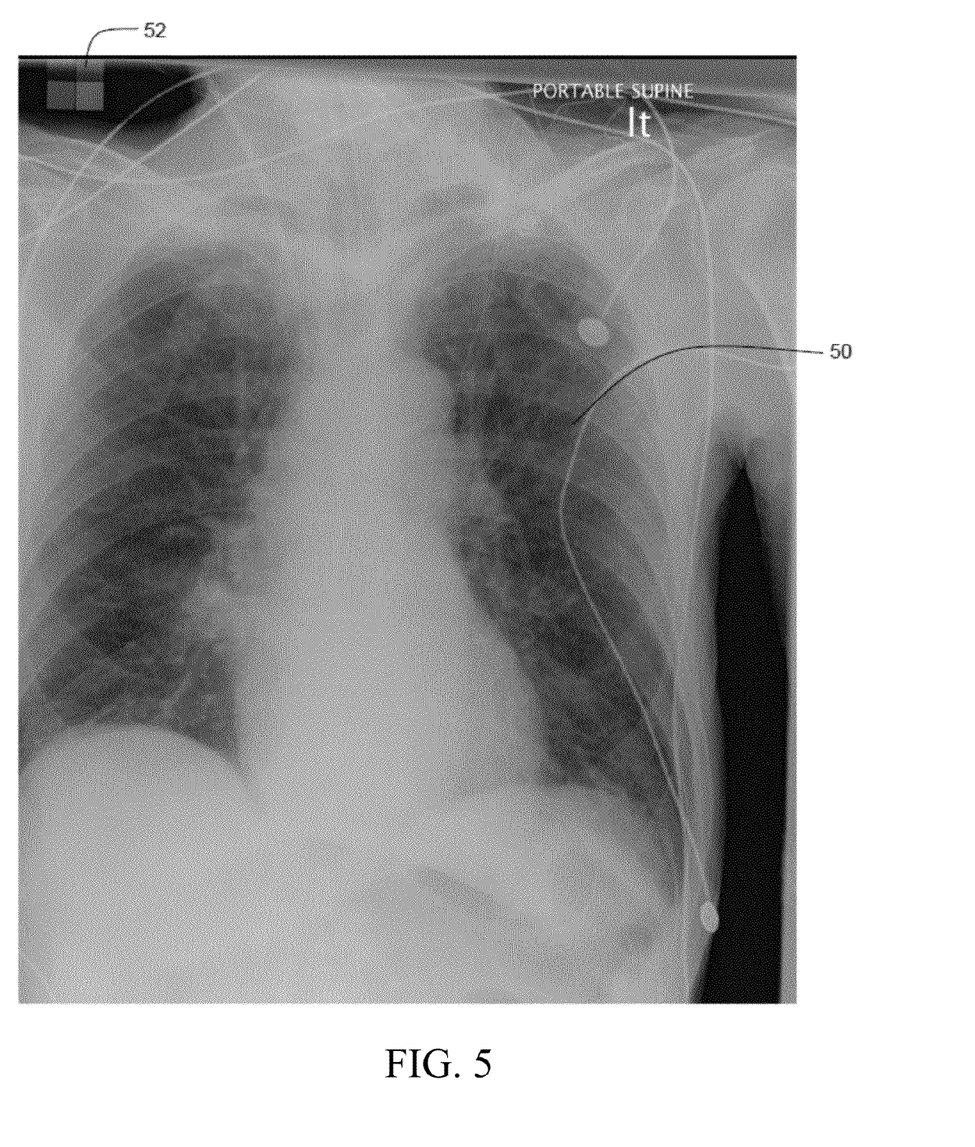
FIG. 5 is a radiographic image containing an embedded image of one embodiment of a variable attenuation plate.
Figure 6:
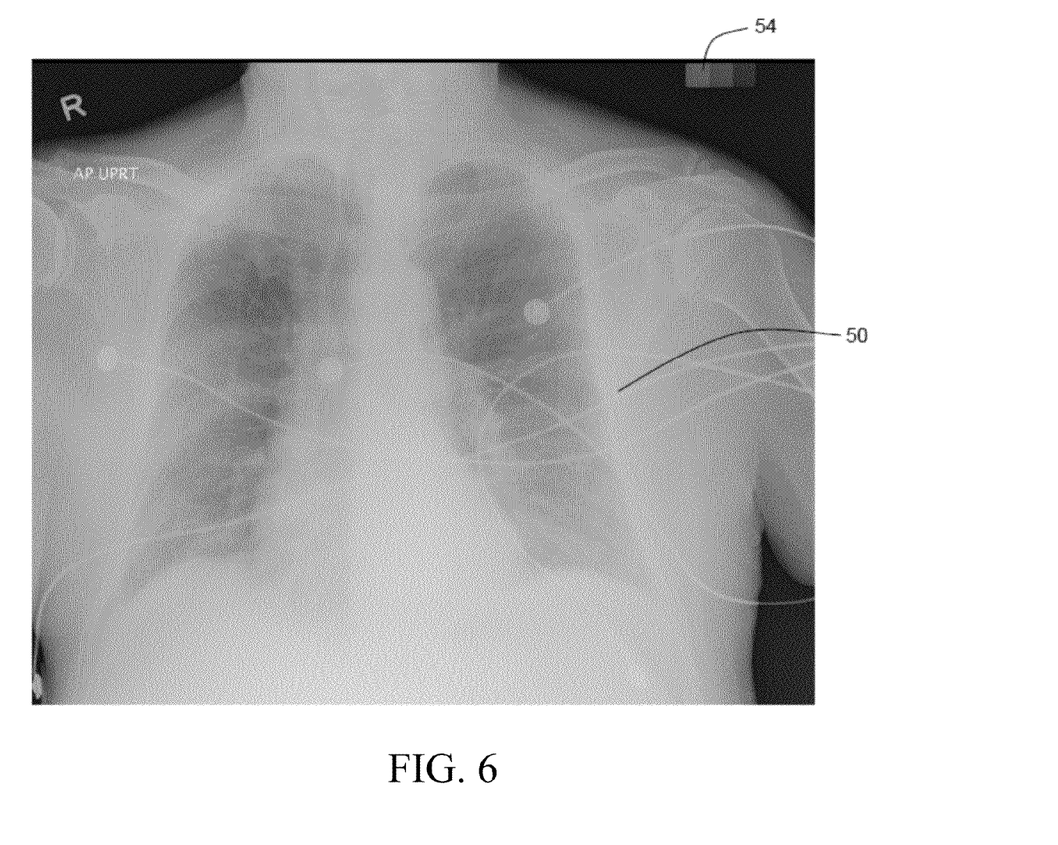
FIG. 6 is another radiographic image containing an embedded image of another embodiment of a variable attenuation plate.

Turning to FIGS. 5 and 6, a test radiographic image 50 including an embedded image 52, 54 of a variable attenuation plate is shown. In this way, a skilled medical professional can extract reference values of contrast and optical density from test radiographic image 50 for comparison to a subsequently recorded radiographic image, or alternatively can use the extracted reference values to form a series of preset reference values for the radiographic equipment, as discussed in detail above.

EXAMPLE

The purpose of this study was to determine whether a novel method that equalizes chest radiograph appearance and allows synchronization of manual windowing with comparison studies, would improve dictating efficiency and radiologist confidence level in interpretation.

The patient population consisted of 50 ICU patients undergoing frontal chest radiographs as part of their medical management. To be included in the study, each patient had to have 2 chest X-rays which included a small variable attenuation plate, placed beside the patient on the film cassette before exposure. The resulting 100 chest radiographs (2 radiographs for each of 50 patients) were placed as acquired into two identical image viewers on a picture archiving and communication system (PACS) with the earlier radiograph to the right of the more recent study. One viewer allowed dictation in the usual manner. The other viewer had specifically designed software which utilized the variable attenuation plate to equalize the appearance of the patients' previous and recent chest X-rays and allow synchronization of manual windowing when comparing studies.

Three thoracic radiologists reviewed and dictated the 50 sets of chest X-rays in each viewer. Each report included an impression of whether the recent radiograph showed improvement, worsening or no change in edema or infiltrates. The sequence of dictation was alternated between cases with radiographs taken with the variable attenuation plate and those without. The total time needed to report all 50 cases in each viewer was monitored along with the actual dictating time per case. The three radiologists completed a specifically designed survey to assess confidence level in their interpretation.

Each of the 3 radiologists dictated all 50 cases in each viewer. One case interpretation by one radiologist was unable to be used due to dictation difficulties. The average total time to report the 50 cases was 20 minutes faster using the variable attenuation plate/software (97 minutes vs. 77 minutes). The average time required to dictate each case was equal at 44 seconds/case. The time needed to report, read or interpret each case (total time minus dictating time) was 20 minutes less with the variable attenuation plate (60 minutes vs. 40 minutes). There was total agreement on all 6 impressions for each case in 23 of 49 cases. The agreement in final impressions between all three radiologists when NOT utilizing the variable attenuation plate cases was 27 of 49 (55%). The agreement in final impressions between the three radiologists when utilizing the software/variable attenuation plate was 38 of 49 (78%). The difference in agreement between the two methods is statistically significant ($X^2$=5.5, p=0.02). On survey, the radiologists were more satisfied with the novel method using the variable attenuation plate then with the previously used conventional method.

The study demonstrated a greater than 20% total time savings when using the variable attenuation plate and associated software over the conventional method. More importantly, the new method resulted in a 23% increase in consistency in report interpretation in this study. Overall, radiologist satisfaction was improved with the new method.

The embodiments described herein are examples of structures, systems or methods having elements corresponding to elements of the techniques of this application. This written description may enable those skilled in the art to make and use embodiments having alternative elements that likewise correspond to the elements of the techniques of this application. The intended scope of the techniques of this application thus includes other structures, systems or methods that do not differ from the techniques of this application as described herein, and further includes other structures, systems or methods with insubstantial differences from the techniques of this application as described herein.

Moreover, the previous detailed description is provided to enable any person skilled in the art to make or use the present invention. Various modifications to those embodiments will be readily apparent to those skilled in the art, and the generic principles defined herein may be applied to other embodiments without departing from the scope of the invention as described herein. Thus, the present invention is not intended to be limited to the embodiments shown herein, but is to be accorded the full scope consistent with the claims, which should be given the broadest interpretation consistent with the description as a whole, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims, which should be given the broadest interpretation consistent with the description as a whole. Moreover, nothing disclosed herein is intended to be dedicated to the public regardless of whether such disclosure is explicitly recited in the claims.

The invention claimed is:

1. A method of comparing a first radiographic medical image with a second radiographic medical image, comprising:
    recording a first radiographic medical image of a patient including a first image of a variable attenuation plate;
    recording a second radiographic medical image of the patient including a second image of the variable attenuation plate;
    determining optical density and contrast reference values from the first and second images of the variable attenuation plate; and
    standardizing the first radiographic medical image and the second radiographic medical image against the optical density and contrast reference values such that the first radiographic medical image can be compared to the second radiographic medical image.

2. A variable attenuation plate for use in the method of claim 1, the variable attenuation plate comprising:
    at least two variable attenuation regions, each of the at least two variable attenuation regions having a different radiographic attenuation;
    wherein when a first radiographic medical image of a patient including a first image of a variable attenuation plate is recorded and a second radiographic medical image of the patient including a second image of the variable attenuation plate is recorded, the first image of the variable attenuation plate and the second image of the variable attenuation plate each comprises an image of each of the at least two variable attenuation regions;
    wherein, in each of the first and second images of the variable attenuation plate, an image of any one of the at least two variable attenuation regions has an optical density which is different from an optical density of an image of at least one other of the at least two variable attenuation regions.

3. The variable attenuation plate of claim 2, further comprising a handle.

4. The variable attenuation plate of claim 2, further comprising a clip for attaching the variable attenuation plate to a radiographic cassette.

5. The variable attenuation plate of claim 2, further comprising one or more indicia of an x-ray marker.

6. A computer for use in the method of claim 1, wherein the computer comprises:

a processor; and a memory coupled to the processor;

wherein the computer is configured to:

determine optical density and contrast reference values from a first image of a variable attenuation plate in a first radiographic medical image of a patient and from a second image of the variable attenuation plate in a second radiographic image of the patient; and     standardize the first radiographic medical image and the second radiographic medical image against the optical density and contrast reference values such that the first radiographic medical image can be compared to the second radiographic medical image.

7. The computer of claim 6, wherein the computer is further configured to carry out radiographic image processing functions.

8. The computer of claim 7, wherein the radiographic image processing functions comprise windowing, manipulation of single images, display of single images, simultaneous manipulation of two or more images, simultaneous windowing of two or more images, simultaneous display of two or more images, or combinations thereof.

9. A non-transitory computer-readable storage medium for use in the method of claim 1, wherein the non-transitory computer-readable medium comprises computer-executable instructions for:

determining optical density and contrast reference values from a first image of a variable attenuation plate in a first radiographic medical image of a patient and from a second image of the variable attenuation plate in a second radiographic image of the patient; and     standardizing the first radiographic medical image and the second radiographic medical image against the optical density and contrast reference values such that the first radiographic medical image can be compared to the second radiographic medical image.

10. The non-transitory computer-readable storage medium of claim 9, further comprising executable instructions to carry out radiographic image processing functions.

11. The non-transitory computer-readable storage medium of claim 10, wherein the radiographic image processing functions comprise windowing, manipulation of single images, display of single images, simultaneous manipulation of two or more images, simultaneous windowing of two or more images, simultaneous display of two or more images, or combinations thereof.

* * * * *